United States Patent
Gong et al.

(10) Patent No.: US 10,365,207 B2
(45) Date of Patent: Jul. 30, 2019

(54) METHOD OF AUTOMATICALLY MODIFYING IMAGING RANGE IN BIOLOGICAL SAMPLE MICROSCOPIC IMAGING

(71) Applicant: WUHAN OE-BIO CO., LTD., Wuhan, Hubei (CN)

(72) Inventors: Hui Gong, Hubei (CN); Jing Yuan, Hubei (CN); Xiaoyu Zhang, Hubei (CN); Qiuyuan Zhong, Hubei (CN)

(73) Assignee: WUHAN OE-BIO CO., LTD., Wuhan (CN)

( * ) Notice: Subject to any disclaimer, the term of this patent is extended or adjusted under 35 U.S.C. 154(b) by 0 days.

(21) Appl. No.: 16/206,697

(22) Filed: Nov. 30, 2018

(65) Prior Publication Data

US 2019/0094129 A1    Mar. 28, 2019

Related U.S. Application Data

(63) Continuation of application No. PCT/CN2017/081166, filed on Apr. 20, 2017.

(30) Foreign Application Priority Data

May 30, 2016  (CN) .......................... 2016 1 0372628

(51) Int. Cl.
*G06K 9/00* (2006.01)
*G01N 21/17* (2006.01)
*G02B 21/36* (2006.01)

(52) U.S. Cl.
CPC ........... *G01N 21/17* (2013.01); *G02B 21/365* (2013.01); *A61B 2576/026* (2013.01);
(Continued)

(58) Field of Classification Search
CPC .............. A61K 49/0008; A61K 31/138; A01K 2217/052; A01K 2227/703; A01K 2267/03
(Continued)

(56) References Cited

U.S. PATENT DOCUMENTS

| 7,403,008 | B2 * | 7/2008 | Blank | .................... | G01R 33/60 |
|           |      |        |       |                      | 324/316    |
| 9,072,772 | B2 * | 7/2015 | Pak   | .................... | A61K 49/0008 |

(Continued)

FOREIGN PATENT DOCUMENTS

| CN | 101276418 A | 10/2008 |
| CN | 101930116 A | 12/2010 |

(Continued)

OTHER PUBLICATIONS

Wang Simin. Study of 3D Neuronal Morphology of Barrel Cortex based on the Golgi-stained Mouse Brain Image Set, Univ Huazhong Science Tech, 2016:1-33.

(Continued)

*Primary Examiner* — Charlotte M Baker
(74) *Attorney, Agent, or Firm* — Wayne & Ken, LLC; Tony Hom

(57) ABSTRACT

A method for automatically altering an imaging area in microscopic imaging of a biological sample. In the method, a sample outline is differentiated from surrounding tissues by means of endogenous or exogenous markers; an initial sample imaging area is set; optical microscopic imaging is performed on a sample surface layer, wherein the imaging area is larger than an area to be imaged of the sample; an actual sample area is calculated by an outline identification algorithm using an imaging result of the sample surface layer and is set as an imaging area of next layer; optical microscopic imaging is performed on a sample to be imaged (Continued)

of the next layer according to the set imaging area, wherein the imaging area covers the area to be imaged of the sample and no redundant imaging is performed; and the above steps are repeated until a data acquisition task is completed.

8 Claims, 2 Drawing Sheets

(52) U.S. Cl.
CPC ............... *G01N 2021/1765* (2013.01); *G01N 2223/427* (2013.01); *G01N 2223/6126* (2013.01)

(58) Field of Classification Search
USPC ......................................................... 382/128
See application file for complete search history.

(56) References Cited

U.S. PATENT DOCUMENTS

| | | | | |
|---|---|---|---|---|
| 9,117,102 | B2* | 8/2015 | Thomas | G06K 9/00134 |
| 9,429,743 | B2* | 8/2016 | Garsha | G02B 21/367 |
| 9,721,751 | B2* | 8/2017 | English | H01J 37/20 |
| 9,810,895 | B2* | 11/2017 | Kimura | G02B 21/002 |
| 2011/0317169 | A1 | 12/2011 | Lin | |
| 2014/0329269 | A1* | 11/2014 | Adey | G01N 1/04 |
| | | | | 435/30 |
| 2018/0120203 | A1* | 5/2018 | Beachley | A01N 1/0263 |

FOREIGN PATENT DOCUMENTS

| | | |
|---|---|---|
| CN | 104075965 A | 10/2014 |
| CN | 105425377 A | 3/2016 |
| CN | 106023225 A | 10/2016 |
| WO | 2013148485 A2 | 10/2013 |

OTHER PUBLICATIONS

Shuntaro Aotake et al., Automated Dynamic Cellular Analysis in Time-lapse Microscopy, Journal of Biosciences and Medicines, 2016:44-50.

* cited by examiner

METHOD OF AUTOMATICALLY MODIFYING IMAGING RANGE IN BIOLOGICAL SAMPLE MICROSCOPIC IMAGING

CROSS-REFERENCE TO RELATED APPLICATIONS

This application is a continuation of International Patent Application No. PCT/CN2017/081166, filed on Apr. 20, 2017, which claims the benefit of priority from Chinese Application No. 201610372628.3, filed on May 30, 2016. The contents of the aforementioned applications, including any intervening amendments thereto, are incorporated herein by reference.

TECHNICAL FIELD

The present disclosure relates to microscopic imaging, and more particularly to a method for automatically altering an imaging area in microscopic imaging of biological samples.

BACKGROUND

It has been long pursued for more image details in a larger imaging area of biological samples in the field of optical imaging. However, imaging of, for example, mice brain of small size requires a day to obtain the whole brain data using optical microscopy in the prior art. Although an interval of axial sampling is omitted, it still takes several days or even more than ten days to obtain a complete fine structure of the brain sample. For larger monkey brain and human brain samples, the imaging time will be greatly increased, thus leading to various instability problems. For example, if the embedding medium for samples is soaked for too long, changes in physical properties of the samples will occur, resulting in deformation, collapse and even fall of the samples. This affects the integrity of data set and consumes a lot of human and material resources. Hence, there is a demand for reduction of redundant data acquisition which can reduce the total acquisition time so as to improve the stability of the imaging system.

Currently, a regular cube is usually employed in the existing optical microscopic imaging system to define an imaging area, i.e., an imaging area that contains a maximum sample area in each transverse coronal plane from top to bottom to ensure the integrity of the whole brain data set. In this manner, a large number of redundant data is acquired, reducing the acquisition efficiency and extending the acquisition time. At the same time, the retention of redundant data takes up a lot of space used to store data.

Some microscopic imaging systems reduce the acquisition of redundant data using manual modification of imaging areas. However, this results in three problems: first, manual modification requires a lot of labor due to a long imaging time; second, it is difficult to realize real-time modification, and the imaging areas are usually altered at a fixed interval so the redundant data still exists; third, it is prone to incorrectly operate and cause system error, resulting in data loss.

Therefore, there exists some defects in manual modification for microscopic imaging area of the biological samples, such as consumption of human resources, difficulty in real-time modification and misoperation. In addition, the existing automatic modification for microscopic imaging area of the biological samples has problems such as high error rate and lack of self-checking ability. Thus, it is necessary to propose a novel method for automatically altering the imaging area in the microscopic imaging of the biological samples.

SUMMARY

An object of the present disclosure is to provide a method for automatically altering an imaging area in microscopic imaging of a biological sample.

The method includes the following steps:

(1) labeling an outline of the biological sample to differentiate the biological sample from a surrounding embedding medium;

(2) setting an initial sample imaging area; imaging a sample surface layer using optical microscopy; wherein the initial sample imaging area is larger than an area to be imaged of the biological sample;

(3) calculating an actual sample area using an outline identification algorithm based on an imaging result of the sample surface layer and setting the actual sample area as an imaging area of a next layer;

(4) imaging a sample to be imaged of the next layer using optical microscopy based on the imaging area of the next layer set at step (3); wherein the imaging area of the next layer covers the area to be imaged of the biological sample, and there is no redundant imaging;

(5) repeating steps (3) and (4) until data acquisition is completed. The present disclosure has the following advantages:

(1) the above steps can be automatically operated by computer softwares; the imaging area can be automatically adjusted according to the imaging result in real time; and a redundant acquisition of the sample is reduced;

(2) whether an outline identification is correct can be judged automatically, so that an error rate can be reduced.

DETAILED DESCRIPTION OF EMBODIMENTS

The present disclosure will be further described below with reference to specific embodiments.

Figure 1:
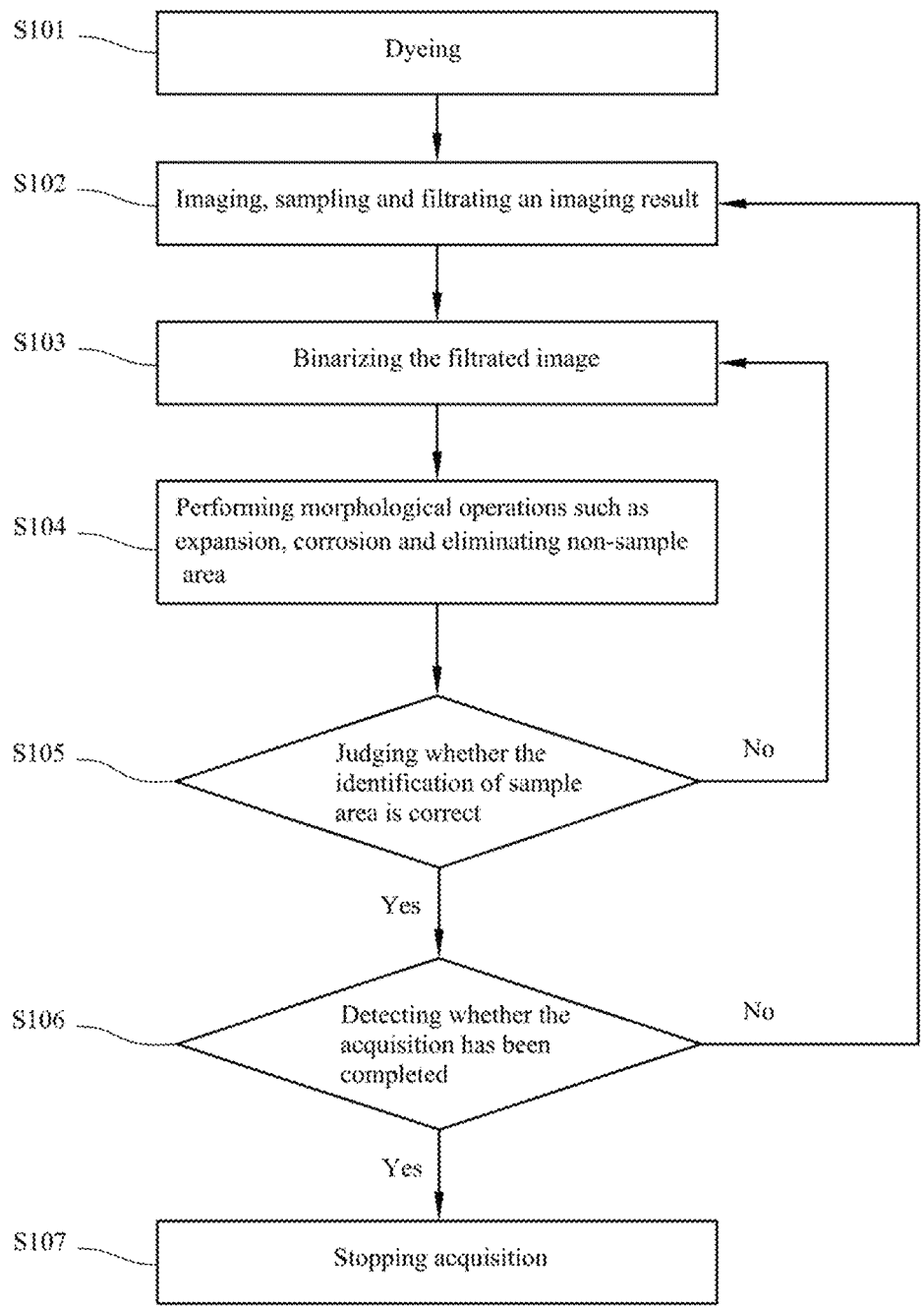
FIG. 1 is a flow chart of a method for automatically altering an imaging area in microscopic imaging of a biological sample.

FIG. 1 is a flow chart of a method for automatically altering an imaging area in microscopic imaging of a biological sample. Particularly, The method includes the following steps:

S101: Labeling an outline of the biological sample by an endogenous or exogenous marker to differentiate the biological sample from a surrounding embedding medium. For example, the biological sample is dyed by a dye or other labeling methods, so that cells in the biological sample are enabled to emit enough signals used to differentiate an effective sample area from the embedding medium.

S102: Imaging a sample surface layer using an optical microscopic imaging system according to a set imaging area; sampling and filtering the imaging result of the sample surface layer if necessary. For example, an average filtering or a median filtering is adopted to reduce effects caused by pattern noise.

S103: Setting a threshold according to sample type; binarizing the filtered image to obtain the effective sample area.

S104: Performing morphological operations of expansion, corrosion and area filling on the binarized image; eliminating non-sample area and retaining the effective sample area if necessary, so that a fluorescence signal emitted by the embedding medium is differentiated from a signal from the effective sample area. If physical properties of the embedding medium change a little in the imaging process, the morphological operations of expansion, corrosion and area filling to eliminate the non-sample area are unnecessary.

S105: Judging whether the effective sample area is correct. If the effective sample area is not correct, altering the threshold according to error type and returning to S104; if the effective sample area is correct, proceeding to next step. Specifically, if a boundary of the identified sample area overlaps with a boundary of the imaging area, the threshold for binarization is increased before returning to S104; if the number of the identified sample area is greater than the actual number of possible sample areas or no effective sample area is identified, the threshold for binarization is reduced before returning to S104; otherwise S106 is executed. The thresholds can be set as various values corresponding to the sample type, or all possible thresholds can be calculated, and the thresholds where an area change of the effective sample area is less than 1% are averaged. Due to a great difference in brightness between the sample area and the non-sample area, appropriate thresholds of the sample can be determined according to the area change of the effective sample area.

S106: Detecting whether the data acquisition has been completed, if not, returning to S102 to continue imaging, otherwise, proceeding to next step.

S107: Stopping acquisition.

Figure 2:
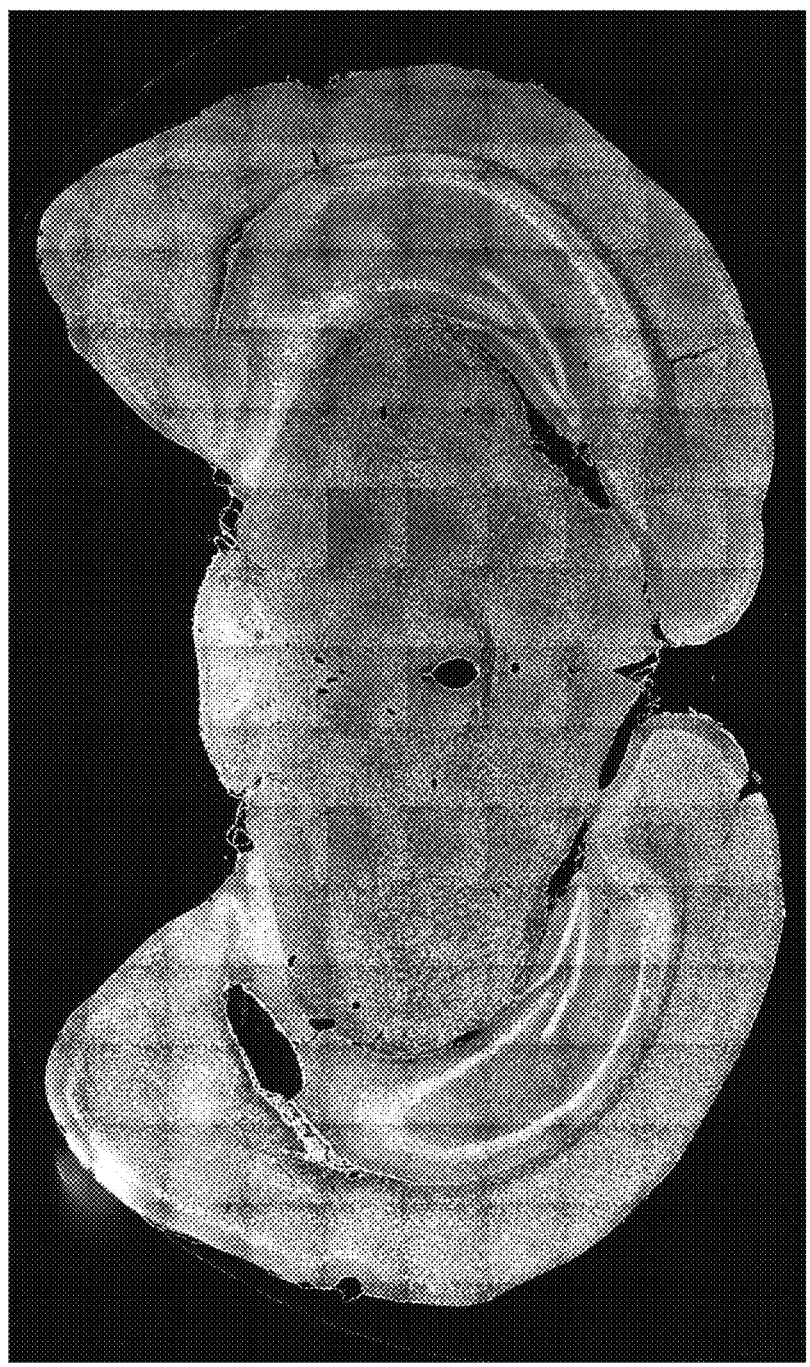
FIG. 2 shows an imaging area of the biological sample identified and determined by the method of the present invention.

The above operation process can be automatically operated by computer softwares. FIG. 2 shows an imaging area of the biological sample identified and determined by the method of the above embodiment. In this embodiment, PI is adopted to dye a mouse brain to obtain an outline information of the sample. The sample acquired by a structured light system undergoes median filtering of 5*5, and then a 8-bit image is binarized with a threshold of 20. After eliminating trivial areas in the binarized image, the expansion and area filling are performed, and then the corrosion is performed three times. Templates are all rectangles with a length of 20. After eliminating areas whose gravities are far from a center of the 8-bit image, the expansion operation were performed two times, and the imaging area is restored back to an original size. Then the effective sample area is obtained. In FIG. 2, a white outline is used to represent the effective sample area, which is used as a acquisition area of a next layer of the sample. It can be seen that this method can effectively identify the sample areas, reduce an acquisition of redundant mosaics, and avoid the negative effect of a extension of acquisition time caused by the acquisition of redundant data. At the same time, the method is short time consuming and can meet the requirements of real-time modification area.

It can be appreciated that for one of ordinary skill in the art, improvements or variations can be made based on the above descriptions, and these improvements and variations fall within the scope of the appended claims.

The embodiments are only illustrative of the present disclosure, and apparently the implementations are not limited by the above modes. The embodiments described herein and various modifications based on the spirit of the present disclosure fall within the scope of the present application.

What is claimed is:

1. A method for automatically altering an imaging area in microscopic imaging of a biological sample, comprising:
    (1) labeling an outline of the biological sample to differentiate the biological sample from a surrounding embedding medium;
    (2) setting an initial sample imaging area; imaging a sample surface layer using optical microscopy; wherein the initial sample imaging area is larger than an area to be imaged of the biological sample;
    (3) calculating an actual sample area using an outline identification algorithm based on an imaging result of the sample surface layer and setting the actual sample area as an imaging area of a next layer;
    (4) imaging a sample to be imaged of the next layer using optical microscopy based on the imaging area of the next layer set at step (3); wherein the imaging area of the next layer covers the area to be imaged of the biological sample, and there is no redundant imaging;
    (5) repeating steps (3) and (4) until data acquisition is completed.

2. The method of claim 1, wherein the outline identification algorithm in step (3) further comprises:
    (a) filtering the imaging result of the sample surface layer;
    (b) setting a threshold according to sample type, binarizing the filtered image to obtain an effective sample area; and
    (c) judging whether the effective sample area is correct; if the effective sample area is not correct, altering the threshold according to error type and returning to step (b); if the effective sample area is correct, proceeding to next step.

3. The method of claim 2, wherein morphological operations of expansion, corrosion and area filling are performed on the binarized image and non-sample area is eliminated, so that a fluorescence signal emitted by the embedding medium is differentiated from a signal from the effective sample area.

4. The method of claim 2, wherein the step of setting the threshold according to sample type comprises setting various thresholds corresponding to the sample type; or, calculating all possible thresholds and averaging the thresholds with an area change of the effective sample area less than 1%; or, determining appropriate thresholds of the sample according to the area change of the effective sample area.

5. The method of claim 3, wherein the step of setting the threshold according to sample type comprises setting various thresholds corresponding to the sample type; or, calculating all possible thresholds and averaging the thresholds with an area change of the effective sample area less than 1%; or, determining appropriate thresholds of the sample according to the area change of the effective sample area.

6. The method of claim 4, wherein the threshold for binarization is increased if a boundary of the identified sample area overlaps with a boundary of the imaging area.

7. The method of claim 4, wherein the threshold for binarization is reduced if the number of the identified sample area is greater than actual number of possible sample area.

8. The method of claim 4, wherein the threshold for binarization is reduced if no effective sample area is identified.

* * * * *